(12) United States Patent
Blanchat et al.

(10) Patent No.: US 6,946,443 B2
(45) Date of Patent: *Sep. 20, 2005

(54) BIOMATERIAL BASED ON AN INSOLUBILIZED DEXTRAN DERIVATIVE AND A GROWTH FACTOR

(75) Inventors: Cinderella Blanchat, Margency (FR); Delphine Logeart-Avramoglou, Groslay (FR); Hervé Petite, Paris (FR); Alain Meunier, Saint-Mandé (FR); Frédéric Chaubet, Eaubonne (FR); Jacqueline Jozefonvicz, Lamorlaye (FR); Marcel Jozefowicz, Lamorlaye (FR); Laurent Sedel, Jouy en Josas (FR); José Correia, Saint Amand les Eaux (FR)

(73) Assignee: Biodex (FR)

(*) Notice: Subject to any disclaimer, the term of this patent is extended or adjusted under 35 U.S.C. 154(b) by 78 days.

This patent is subject to a terminal disclaimer.

(21) Appl. No.: 10/016,706

(22) Filed: Dec. 11, 2001

(65) Prior Publication Data

US 2002/0169120 A1 Nov. 14, 2002

(51) Int. Cl.$^7$ .................... A61K 38/18; A61K 31/721
(52) U.S. Cl. ............................... 514/12; 514/59
(58) Field of Search ...................... 514/59, 12

(56) References Cited

FOREIGN PATENT DOCUMENTS

| FR | 2 722 982 | 6/1990 |
|---|---|---|
| FR | 2 644 066 | 9/1999 |
| WO | WO 89/12464 | 12/1989 |
| WO | WO 90/10456 | 9/1990 |
| WO | WO 95/2678 | 10/1995 |
| WO | WO 99/01143 | 1/1999 |

OTHER PUBLICATIONS

International PCT Patent Application No. PCT/FR00/01603, filed Jun. 9, 2000, International Publication No. WO 00/76562 A1, published Dec. 21, 2000 (English Translation).

PCT International Search Report for International PCT Patent Application No. PCT/FR00/01603, filed Jun. 9, 2000, International Publication No. WO 00/76562 A1, published Dec. 21, 2000.

PCT Chapter II Demand (Avis Informant Le Deposant De La Communication De La Demande Internationale Aux Offices Designes) for International PCT Patent Application No. PCT/FR00/01603, filed Jun. 9, 2000, International Publication No. WO 00/76562 A1, published Dec. 21, 2000.

Notification of Countries Elected (Informations Relatives Aux Offices Elus Qui Ont Recu Notification De Leur Election) for International PCT Patent Application No. PCT/FR00/01603, filed Jun. 9, 2000, International Publication No. WO 00/76562 A1, published Dec. 21, 2000.

Notification of Change of Applicant (Notification De L'Enregistrement D'Un Changement) for International PCT Patent Application No. PCT/FR00/01603, filed Jun. 9, 2000, International Publication No. WO 00/76562 A1, published Dec. 21, 2000.

PCT Preliminary International Examination Report (Rapport D'Examen Preliminaire International) for International PCT Patent Application No. PCT/FR00/01603, filed Jun. 9, 2000, International Publication No. WO 00/76562 A1, published Dec. 21, 2000.

Abstract: Japanese Application No. 04075920 filed Feb. 28, 1992, Publication No. 05238930 published Sep. 17, 1993 of Eisai Co., Ltd., pertains to a Long–Acting Medicine.

Publication: "*In vitro relase characteristics of bioactive molecules from dextran dialdehyde cross–linked gelatin hydrogel films*" by Jean–Pierre Draye, Bernard Delaey, Andre Van de Voorde, An Van Den Bulcke, Bogdan Bogdanov, and Etienne Schacht of Ghent, Belgium, Biomaterials published by *Elsevier Science, Ltd.* 1998.

*Primary Examiner*—James O. Wilson
*Assistant Examiner*—Ganapathy Krishnan
(74) *Attorney, Agent, or Firm*—Welsh & Katz, Ltd.; Thomas W. Tolpin

(57) ABSTRACT

The invention concerns a biologically active material essentially comprising at least an insolubilized dextran derivative of general formula $DMC_aB_bSU_cS_d$ and at least a growth factor having an activity on osteoarticular, dental and/or maxillofacial tissues, and the method for preparing same. The invention also concerns the uses of said biomaterial for preparing a repair or filing material, such as an implant, for osteoarticular, dental or maxillofacial applications and for preparing an orthopaedic, dental or maxillofacial prosthesis, and the prosthesis coated with said biologically active material.

21 Claims, 4 Drawing Sheets

BIOMATERIAL BASED ON AN INSOLUBILIZED DEXTRAN DERIVATIVE AND A GROWTH FACTOR

CROSS REFERENCES TO RELATED APPLICATIONS

This application is based upon priority International Application PCT/FR00/01603 filed Jun. 9, 2000, International Publication No. WO 00/76562 A1 published Dec. 21, 2000, which is based upon priority French patent application 99/07401 filed Jun. 11, 1999.

BACKGROUND OF THE INVENTION

The present invention relates to a biomaterial, to the process for its preparation and to its applications, in particular as repair or filling material in the osteoarticular, dental or maxillofacial field.

To consolidate bone defects, methods commonly used are autografting or allografting. Corticospongy autografting is the oldest method: it makes it possible to obtain good quality bone consolidation with perfect immune tolerance and with no risk of transmission of pathogenic agents. However, the bone stock is limited in an individual, especially in children, and the additional surgical act which results therefrom causes risks of complications. As for the allograft, which is removed from subjects in a state of cerebral death, it only exhibits osteoconductive and nonosteoinductive properties since the bone removed is frozen so as to destroy all the components which could trigger an immune reaction of graft rejection by the recipient body or could be a vector of infections. This treatment reduces, in addition, the mechanical properties of bone.

By virtue of the insufficiency of bone grafts, bone replacement materials are currently the essential research route for promoting bone consolidation.

These materials are of considerable public health importance. Indeed, numerous synthetic or metallic materials are used as bone replacement materials in indications as diverse as bone graft or total hip prosthesis. Currently, 60 000 total hip prostheses are implanted each year in France. In 1988, an epidemiological study showed that half of the implants fitted in 16 million American patients were orthopedic implants. These statistics can be extrapolated to the French situation.

Bone consolidation involves various types of cell derived either from the mesenchymal line (preosteoblasts, osteoblasts and osteocytes), or from the hematopoietic line (osteoclasts). The osteoblasts, which are located at the bone surface, are involved in the synthesis of a novel bone matrix. The osteocytes are included in the bone matrix; connected to each other, they form a true intercellular network. The osteoclasts, which make it possible to resorb the bone, are dependent on growth factors. The osteoclastic activity is essential for reconstruction, because it is itself capable of amplifying the activities of synthesis of osteoblasts by means, inter alia, of growth factors. The platelets also have an important role: they release large quantities of growth factors, at the initial stage of bone repair.

Growth factors are a category of polypeptides having properties which regulate numerous parameters of cell life (such as proliferation, differentiation, survival). These factors are secreted by multiple types of cell. The effects of the same factor are determined by the nature of the target cell, the concentration of the factor, the possible simultaneous presence of other factors. The target cells possess membrane receptors for these factors, most often tyrosine kinases. Their stimulation regulates the synthesis or the activity of regulatory proteins. The names of the growth factors are most often taken from the material where they were detected for the first time and are not always representative of their function.

Bone tissue contains a variety of growth and differentiation factors which control bone formation and resorption and which also play an important role in the development, growth and repair of cartilage and bone. These principal factors are EGFs ("Epidermic Growth Factors"), IGFs ("Insulin-like Growth Factors"), FGFs ("Fibroblast Growth Factors"), TGF-$\beta$ ("Transforming Growth Factors"), PDGFs ("Platelet-Derived Growth Factors") and BMPs ("Bone Morphogenetic Proteins").

The BMPs are part of the TGF-$\beta$ superfamily. Their osteoinductive activity was demonstrated by M. R. Urist in 1965 (Science, 1965, 150, 893–899): demineralized bone was implanted at an ectopic, namely intramuscular, site in rats and gave rise to the formation of cartilage, and then bone. The proteins extracted from the demineralized bone and which are responsible for this bone induction were purified and called Bone Morphogenetic Proteins (BMP). Seven proteins (BMP-1 to 7) were initially cloned using molecular biology techniques (Wozney, J. M. et al., Science, 1988, 242, 1528–1534). It has since been shown that BMP-1 does not have osteoconductive properties. To date, numerous other BMPs have been cloned.

The use of BMPs alone in bone repair involves the injection of large quantities, much higher than those effective in in vitro studies or detected in normal tissues.

Moreover, the systemic effect of these products exhibits risks of diffusion of BMP into the surrounding muscle mass and of local calcification in a non-bone site. In addition, BMPs have very short lives, of the order of a few minutes in free form.

It would therefore be desirable to develop a vector for BMPs as well as for the other growth factors involved in bone repair.

T. R. Gerhart et al. (Clinical orthopaedics and related research, 1993, 293, 317–326 and 1995, 318, 222–230) have proposed mixing human recombinant BMP-2 with inactive bone matrix (1.5 mg of BMP per 3 g of bone matrix) in order to produce bone implants. These implants make it possible to induce reossification of defects 2.5 cm long artificially created in the femurs of sheep. However, the quantity of BMP provided by the implant (1.5 mg) is 25 000 times higher than the quantity of BMP endogenously present in the native bone tissues (~0.06 $\mu$g).

Other types of supports have also been proposed: collagen, hydroxyapatite, gelatin, tricalcic calcium phosphate, calcium sulfate, calcium carbonate, coral, polymers of polylactic and polyglycolic acids, and the like.

All these organic or inorganic, natural or synthetic compounds are not really vectors for BMP. They indeed exhibit affinity which is good to a greater or lesser degree with the growth factor.

In parallel with these studies, it has been shown that, in a manner similar to heparin and to heparan sulfates, dextrans (D) substituted with carboxymethyl (MC), benzylamide (B) and sulfonate (S) groups (compounds called DMCBS) interact with certain growth factors, HBGFs (Heparin Binding Growth Factors), in particular with FGFs and TFG-$\beta$. They potentiate the biological effects of these endogenous factors, released at the lesioned site, protecting them against degradations of thermal, acidic or proteolytic origin (F. Blanquaert et al., Bone, 1995, 17, 6, 499–506; A. Meddahi et al., Journal of Biomedical Materials Research, 1996, 31, 293–297; J. Lafont et al., Growth factors, 1998, 16, 23–38; F. Blanquaert et al., Journal of Biomedical Materials Research, 1999, 44, 63–72).

In the field of bone repair, particular CMDBSs, RGTA9 and RGTA11 (compounds comprising respectively 83% or 110% of CM units, 23% or 2.6% of B units and 13% or 36.5% of S units), immobilized in a collagen support, have made it possible to induce bone regeneration (abovementioned articles by F. Blanquaert et al., 1995 and J. Lafont et al., 1996). It has thus been shown that RGTA9 and RGTA11 themselves, without addition of exogenous growth factors, make it possible to stimulate bone reconstruction. F. Blanquaer et al., 1995, explain this property by the fact that RGTA9, which is vectorized in collagen and complexed with the growth factors endogenously present, could constitute a reservoir of said growth factors for their subsequent release. J. Lafont et al. propose using RGTA11 as such, transported in a collagen support, instead of administering growth factors.

In short, F. Blanquaert et al. and J. Lafont et al. therefore propose vectorizing RGTA9 or RGTA11 in a collagen support, which is known to induce a rapid and uncontrolled kinetics of release.

Moreover, the abovementioned article by F. Blanquaert et al. (1999) describes the stimulation of the expression of the osteoblastic phenotype by RGTA9 and RGTA11 placed in contact, in vitro and in soluble form, with growth factors (BMP-2, TGF-β1, FGF-2). It is indicated that this effect results from a capacity of the RGTAs to interact with these growth factors, thus making it possible to promote the wound healing process. It is also indicated that RGTA9 is less effective than RGTA11, both compounds essentially differing in terms of their respective degrees of substitution with sulfonate groups (S), namely 0.13 for RGTA9 and 0.365 for RGTA11. It is evident from these results that a high percentage of S units plays an important role in the properties of the dextran derivative on bone repair.

Thus, the various abovementioned articles (F. Blanquaert et al., 1995 and 1999; A. Meddahi et al., 1996; J. Lafont et al., 1998) show that the DMCBS are capable of trapping these endogenously released growth factors; they play the role of a temporary reservoir for growth factors which are naturally secreted at the lesioned site.

Such combinations between the DMCBSs and the growth factors, which are formed in vivo, do not constitute an effective vector for said growth factors for use in surgery, in particular in spinal, maxillofacial or dental surgery, or any reconstructive surgery. Indeed, their soluble form does not make it possible to control the diffusion of the growth factors at a specific site. In addition, these combinations do not make it possible to restore the geometry of the bone pieces destroyed, in particular of large bone defects, in which the endogenous growth factors are not present in a sufficient quantity to be able to initiate spontaneous consolidation. It is then necessary to add exogenous growth factors, which have to be used in vivo in combination with a suitable releasing system.

BRIEF SUMMARY OF THE INVENTION

The inventors set themselves the aim of providing a support material for growth factors, in particular BMPs, which meets the following requirements:

it is provided in solid form, it is suitable for the reconstruction of large losses of osteoarticular substance, in particular for the reconstruction of bone defects, it exhibits a real affinity for the growth factor, it makes it possible to control the kinetics of release of the growth factor, it makes it possible to control the location of release of the growth factor, avoiding its diffusion in an extrabone site, it makes it possible to control the local concentration of growth factor released, it does not exhibit mutagenic activity, it is biocompatible, nonimmunogenic, nontoxic and biodegradable, it protects the bioactive molecule, without denaturing it, it makes it possible, in addition, to reduce the quantity of BMP used.

The subject of the present invention is a biomaterial characterized in that it essentially comprises:

at least one insolubilized dextran derivative of general formula $DMC_a B_b Su_c S_d$ in which:

1. D represents a polysaccharide chain, preferably consisting of successions of glucoside units, MC represents methyl carboxylate groups, B represents carboxymethylbenzylamide groups, Su represents sulfate groups (sulfation of the free hydroxyl functional groups carried by the glucoside units), S represents sulfonate groups (sulfation of the aromatic rings of the B groups), a, b, c and d represent the degree of substitution (ds), expressed relative to the number of free hydroxyl functional groups in a glucoside unit of the dextran, respectively in MC, B, Su and S groups; $a \geq 0.3$, b being equal to 0 or $\geq 0.2$, c being equal to 0 or $\geq 0.1$ and d being equal to 0 or $\leq 0.15$, provided that when b is equal to 0, c is not equal to 0, and 2. at least one growth factor exhibiting activity on the osteoarticular, dental and/or maxillofacial tissues.

The expression "growth factor exhibiting activity on the osteoarticular, dental and/or maxillofacial tissues" is understood to mean a growth factor involved in the processes of wound healing and of reconstruction of bones, but also of the tendons, ligaments and the like.

The dextran derivatives described above are considered as being copolymers consisting of fictitious subunits R—OH and R—OX, it being possible for X to be a methyl carboxylate, benzylamide, sulfate or sulfonate group, the polysaccharide chain of the unsubstituted dextran being considered to consist of 300 fictitious R—OH subunits, instead of 100 glucoside units, in the light of the fact that an unsubstituted glucoside unit comprises three free hydroxyl groups. Thus, a dextran methyl carboxylate (DMC) with a degree of substitution (ds) of 1.2 with methyl carboxylate groups contains 1.20 substituted groups (R—C and 1.80 free hydroxyl groups (R—OH) per glucoside unit.

The dextran derivatives described above may be prepared by a process which comprises the following steps, depending on the groups present in the dextran derivative:

a) carboxymethylation comprising (i) the activation of an unsubstituted dextran, by bringing said dextran into contact with a basic two-phase aqueous-alcoholic liquid medium for at least 1 h, with stirring, (ii) addition of monochloroacetic acid to the activated product obtained, at a temperature of between 40 and 90° C., preferably at 60° C. the ratio $R_{MC}$, equal to the number of mol of monochloroacetic acid/number of mol of OH, being between 0.3 and 2, (iii) isolation and optionally purification of the dextran methyl carboxylate (DMC) obtained, b) coupling of benzylamine with the methyl carboxylate groups comprising (i) bringing the DMC obtained in a) into contact, for at least 2 h and in acidic aqueous medium, with benzylamine, in the presence of a water-soluble carbodiimide as coupling agent, at a temperature of between 0° C. and 30° C., the water-soluble carbodiimide/MC molar ratio being between 0.25 and 2 and the benzylamine/MC molar ratio being between 0.25 and 2, (ii) the isolation of the dextran methylcarboxyl benzylamide (DMCB) obtained and optionally its purification, c) sulfation comprising (i) the formation of a trialkylammonium salt of the DMCB obtained in b), (ii) the solubilization of the salt obtained in an anhydrous polar solvent, generally a Lewis base, such as dimethyl sulfoxide (DMSO) or dimethylformamide (DMF) and (iii) the addition, to said salt in solution, of a complex based on sulfur trioxide such as $SO_3$-pyridine, $SO_3$-triethylamine or $SO_3$-DMF in solution in the same solvent, at a temperature of less than 70° C., the molar ratio complex based on sulfur trioxide/free OHs being between 0.25 and 12, and d) sulfonation of the B groups by mixing, with stirring, a DMCB derivative obtained in b) or DMCBSu obtained in c) in suspension in an anhydrous solvent with chlorosulfonic acid in solution in the same solvent, at a temperature of between room temperature and the boiling temperature of the solvent used.

In step a), the water:alcohol ratio of said two-phase aqueous-alcoholic liquid medium is for example between 10:90 (v/v) and 25:75 (v/v), and is preferably 15:85 (v/v).

The water-soluble carbodiimide of step b) is for example selected from the group consisting of 1-cyclohexyl-3-(2-morpholinoethyl)carbodiimide meta-p-toluene sulfonate (CMC) and 1-ethyl-3-(3-dimethylaminopropyl) carbodiimide hydrochloride (EDC).

When they are prepared by the process described above, the dextran derivatives present in the biomaterial according to the invention exhibit homogeneity in the distribution of the sizes of the chains, illustrated by an elution profile of the symmetric Gaussian type in high-performance steric exclusion chromatography and homogeneity in the distribution of the charged chemical groups, illustrated by a symmetric single-peak elution profile in low-pressure ion-exchange chromatography.

Preferably, said insolubilized dextran derivative described above is such that d is equal to 0.

The insolubilized dextran derivative present in the biomaterial according to the present invention serves as a vector for said growth factor. Noncovalent interactions (for example of the electrostatic, polar or apolar, or dipole/dipole type Van der Waals bonds, hydrogen or hydrophilic bonds) develop between the growth factor and the dextran derivative.

In a particularly advantageous manner, the biomaterial according to the present invention, which exists in solid form, makes it possible to control the location and the kinetics of release of the growth factor, it thus constitutes a controlled release support material for growth factors.

Preferably, said growth factor is selected from the group consisting of EGFs, IGFs, FGFs, TGF-βs, PDGFs and BMPs.

According to an advantageous feature of this embodiment, said growth factor has an osteoinductive activity. It is preferably a BMP, it being possible for the latter to be a recombinant BMP or to be obtained by a method of extraction. A recombinant BMP may be provided, for example, by genetic engineering using molecular biology techniques known per se, while an extracted BMP may be derived from human or animal tissues, in which case a mixture of proteins is obtained which comprises in particular a mixture of osteoinductive proteins.

Unexpectedly, such a biomaterial is a particularly effective vector for a controlled release in situ of said growth factor.

Indeed, the biomaterial according to the invention is degraded in vivo by the cells of the organism, in particular the macrophages, which allows the release of the growth factor vectorized by the insolubilized dextran derivative.

The biomaterial according to the invention protects and potentiates the effects of the growth factor which is combined with it (exogenous growth factor); it acts as a reservoir for said growth factor and it contributes to its controlled release, in bioavailable form, at the lesioned sites, thus stimulating wound healing and tissue regeneration. The biomaterial according to the invention also protects and potentiates the endogenous growth factors naturally released at the lesioned site.

In the orthopedic field, where the filling out of bone defects of traumatic or tumor origin and the pulling out of implanted prostheses pose difficult problems of reconstruction, such a biomaterial makes it possible, surprisingly, to potentiate bone regeneration in a controlled manner. Such a material is also particularly well suited to spinal surgery (for example for carrying out arthrodeses of the rachis, that is to say joining several vertebrae to each other), to maxillofacial surgery, to dental surgery and to reconstructive surgery.

In a particularly advantageous manner, the biomaterial according to the invention, based on at least one dextran derivative, is biocompatible and does not cause any risk of contamination with pathogenic agents of animal origin.

The biomaterial according to the invention may be advantageously combined with several growth factors involved in the bone reconstruction process. It may also advantageously comprise several insolubilized dextran derivatives corresponding to the general formula $DMC_aB_bSu_cS_d$ as defined above.

According to another advantageous embodiment of said biomaterial, it is insolubilized by crosslinking with the aid of a crosslinking agent.

According to an advantageous feature of this embodiment, said crosslinking agent is selected from the group consisting of sodium trimetaphosphate, epichlorohydrin, divinyl sulfone, glutaraldehyde and bisepoxiranes. By way of example of bisepoxiranes which can be used, there may be mentioned 1,4-butanediol-bis (epoxypropyl) ether and 1,4-butanediol-diglycidyl ether.

All these crosslinking agents make it possible to create bridges between the hydroxyl functional groups of the chains of the dextran derivatives.

According to another advantageous embodiment of said biomaterial, it exists in the form of a hydrogel, or in the form of a freeze-dried powder, said freeze-dried powder being advantageously obtained from the abovementioned hydrogel.

According to another advantageous embodiment of said biomaterial, it comprises, in addition, a tissue filling material.

According to yet another advantageous embodiment of said biomaterial, it coats particles of an inorganic or polymeric insoluble support, said particles having a diameter greater than 100 μm. According to this aspect of the invention, the biomaterial is insolubilized on said particles and exists in a particulate form.

According to an advantageous feature of these embodiments, said tissue filling material is selected from the group consisting of collagen, gelatin, biological adhesive, polymers of polylactic or polyglycolic acids and copolymers of polyethylene glycol and polylactide-co-glycolide.

According to another advantageous feature of these embodiments, said tissue filling material is an osteoconductive material selected from the group consisting of coral, hydroxyapatite, a mixture of collagen and hydroxyapatite, tricalcic calcium phosphate, calcium sulfate and calcium carbonate.

The expression "osteoconductive" is understood to mean a material which serves as a three-dimensional support for vascular regrowth and the growth of osteoprogenitor cells, said material allowing gradual bone regrowth, without being capable of initiating the manufacture of bone at an ectopic site, unlike an "osteoinductive" material which, for its part, stimulates an osteogenic activity by inducing proliferation and differentiation of the cells of the perivascular mesenchyme into osteoprogenitor cells at an ectopic site (M. R. Urist, Science, 1965, 150, 893–899).

The subject of the present invention is also a process for preparing the insolubilized biomaterial by crosslinking as described above, characterized in that it comprises the following steps:

crosslinking of at least one dextran derivative of general formula $DMC_aB_bSu_cS_d$ as described above, adsorption, in the insolubilized dextran derivative obtained above, of at least one growth factor as defined above, production of a biomaterial according to the invention in the form of a hydrogel, optionally, the freeze-drying of said hydrogel in order to obtain the biomaterial according to the invention in the form of a powder.

According to an advantageous embodiment of the process according to the invention, said crosslinking of at least one dextran derivative of general formula $DMC_aB_bSu_cS_d$ is carried out with the aid of a crosslinking agent as described above.

According to another advantageous embodiment of the process according to the invention, said crosslinking of at least one dextran derivative of general formula $DMC_aB_bSu_cS_d$ is carried out in the presence of an osteoconductive filling material as described above.

The subject of the present invention is also a process for preparing the biomaterial in particulate form as described above, characterized in that it comprises the following steps:

bringing the dextran derivative into contact with particles of an inorganic or polymeric insoluble osteoconductive support, as described above, so as to obtain a composite, insolubilization of the composite obtained above, in the presence of a crosslinking agent, adsorption, in the insolubilized composite obtained above, of at least one growth factor as defined above.

The crosslinking agents which can be used in this process are identical to those described above.

The subject of the present invention is also the use of a biomaterial as defined above for the preparation of a repair or filling material for osteoarticular, dental or maxillofacial applications, in particular for the preparation of osteoarticular, dental or maxillofacial implants.

The subject of the present invention is also the use of a biomaterial as defined above for the preparation of a coating for orthopedic, dental or maxillofacial prostheses.

Such a prosthesis, for example, and without limitation, consists of a ceramic, a stainless steel, a titanium alloy or a chromium-cobalt alloy.

The subject of the present invention is, in addition, a functionalized prosthesis, characterized in that at least part of its surface is coated with a biomaterial according to the invention.

According to the preceding features the invention also comprises other features which will emerge from the description which follows, which refers to examples of biomaterials according to the invention and to examples of their use, as well as to the accompanying figures and appended claims.

DETAILED DESCRIPTION OF THE INVENTION

Figure 1:
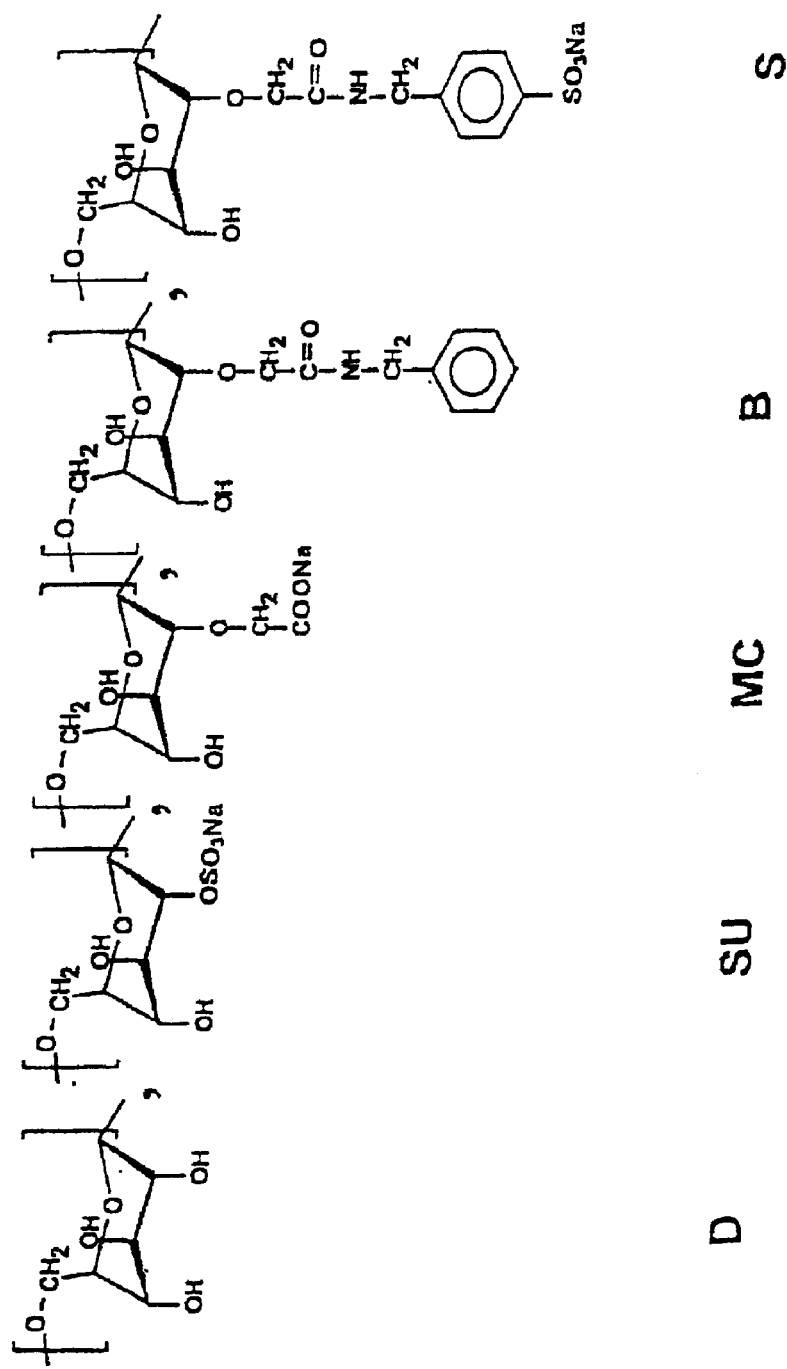
FIG. 1 schematically illustrates the structure of a dextran derivative of general formula $DMC_aB_bSu_cS_d$.

Biomaterial based on an insolubilised dextran derivative and a growth factor according to the preferred embodiments of the present invention will now be explained in view of the following examples. It should however be clearly understood that these examples are given solely by way of illustration of the subject of the invention, and do not constitute in any manner a limitation thereto.

EXAMPLE 1

Demonstration of the Interaction of Various Polymers, of which Several Dextran Derivatives of Formula $DMC_aB_bSu_cS_d$, with the Growth Factor TGF-β1

This example relates to tests for screening polymers, in particular functionalized dextran derivatives comprising units chosen from MC, B, S and Su, as defined above, for selecting polymers having good affinity for TGF-β1.

a) Polymers Used

The structural characteristics of the various polymers used are summarized in table 1 below, the degrees of substitution with CM, B, Su and S groups being indicated for each polymer. The polymer "T40" indicates a native dextran (Pharmacia Fine Chemical, weight-average molar mass $M_w$:

37 500 g/mol, $M_w/M_n$: 1.7, $M_n$ representing the number-average molar mass). The other polymers correspond to functionalized dextran derivatives.

TABLE I

| Polymers | MC | B | Su | S |
|---|---|---|---|---|
| DMC 7 | 1.10 | 0 | 0 | 0 |
| FC 27 | 0.75 | 0.37 | 0.64 | 0 |
| FC 27 EI-1 | 0.65 | 0.33 | 0.63 | 0.02 |
| DMCBS R2 | 0.70 | 0.32 | 0.12 | 0.01 |
| DMCBSu | 0.63 | 0.35 | 1.30 | 0 |
| DMCBS 25 | 0.75 | 0.20 | 0.13 | 0.02 |
| DMCB 2 | 0.75 | 0.37 | 0 | 0 |
| TD4 | 0.76 | 0.31 | 0 | 0 |
| TD5 | 0.64 | 0.43 | 0 | 0 |
| T40-B2 | 0.65 | 0.29 | 0 | 0 |
| LS13 | 0.98 | 0 | 0 | 0 |
| LS4 | 0.67 | 0.33 | 0 | 0 |
| LS5 | 0.81 | 0.23 | 0 | 0 |
| LS8 | 0.59 | 0.39 | 0 | 0 |
| RO5 | 0.70 | 0.35 | 0.8 | 0.01 |
| Van 1 | 0.76 | 0.38 | 0 | 0 |
| Van 2 | 0.75 | 0.37 | 0.64 | 0 |
| Van 3 | 0.74 | 0.37 | 1.08 | 0 | b) Materials and Method 15 ng (0.5 µl) of TGF-β1 (provided by R&D System), alone (control) or in the presence of 100 µg of polymer, are dissolved in 10 µl of sample buffer, namely 125 mM sodium acetate, 50 mM Tris buffer pH 7.00, and 0.5% bovine serum albumin (BSA). The samples are incubated for 1 to 2 h at 4° C.

45 ml of a 0.8% agarose gel are prepared. The samples are loaded onto the agarose gel, on which 2 µl of glycerol at 75% and Bromophenol Blue have been previously deposited. The electrophoreses is carried out for 4 h under a current of 200 mA, at a temperature of 4° C. The migration buffer is a buffer comprising 125 mM sodium acetate and 50 mM Tris-HCl buffer pH 7.00.

At the end of migration, the gel is incubated for 15 to 20 minutes in a transfer buffer comprising 25 mM Tris-HCl buffer pH 9.00, 192 mM glycine, 20% methanol and SDS (sodium lauryl sulfate). The gel is then transferred by capillarity onto a PVDF (polyvinylidene fluoride) membrane previously soaked in methanol and then ultrapure water (3 minutes) and finally in the transfer buffer, the transfer being carried out by capillarity overnight.

The PVDF membrane is then soaked for 20 minutes in a TBS buffer (20 mM Tris-HCl and 150 mM NaCl), 0.05% Tween and 1% BSA mixture, and then for 20 minutes in a TBS buffer, 0.05% Tween and 1% gelatin mixture.

Two membrane incubation steps follow:

from 1 h 30 min to 2 h, at room temperature, with a solution, diluted 1/1000, of primary rabbit anti-TGF-β antibody, provided by Promega (that is 10 µl of antibody in 10 ml of TBS/0.05% Tween/1% BSA). The incubation is followed by washing of the membrane, 4×10 minutes, with a TBS/0.05% Tween solution;

from 1 h to 1 h 30 min, at room temperature, with a solution, diluted 1/2500 of secondary anti-rabbit antibody coupled to peroxidase (Boehringer Mannheim), that is 10 µl of antibody in 25 ml of TBS/0.05% Tween/1% BSA. The incubation is followed by washing of the membrane, 3×10 minutes, with a TBS/1.05% Tween solution, and then a final wash with TBS buffer.

Colorimetric visualization is then carried out. For this purpose, a solution of ortho-dianisidine at 0.5% in methanol (50 mg/10 ml) and a solution of 0.01% hydrogen peroxide/10 mM Tris buffer pH 7.4 are prepared. The colorimetric visualization is carried out by adding to the membrane 50 ml of Tris buffer and 125 µl of the ortho-dianisidine solution (that is 0.00125%). A brown color appears within a few minutes. The calorimetric visualization is then stopped by addition of water.

The growth factor alone (control) should migrate little, its iscelectric point (pI) being close to the pH of the migration buffer; on the other hand, if it forms a complex with a polymer which is strongly anionic, the combination will migrate toward the anode (+).

c) Results

Figure 2A:
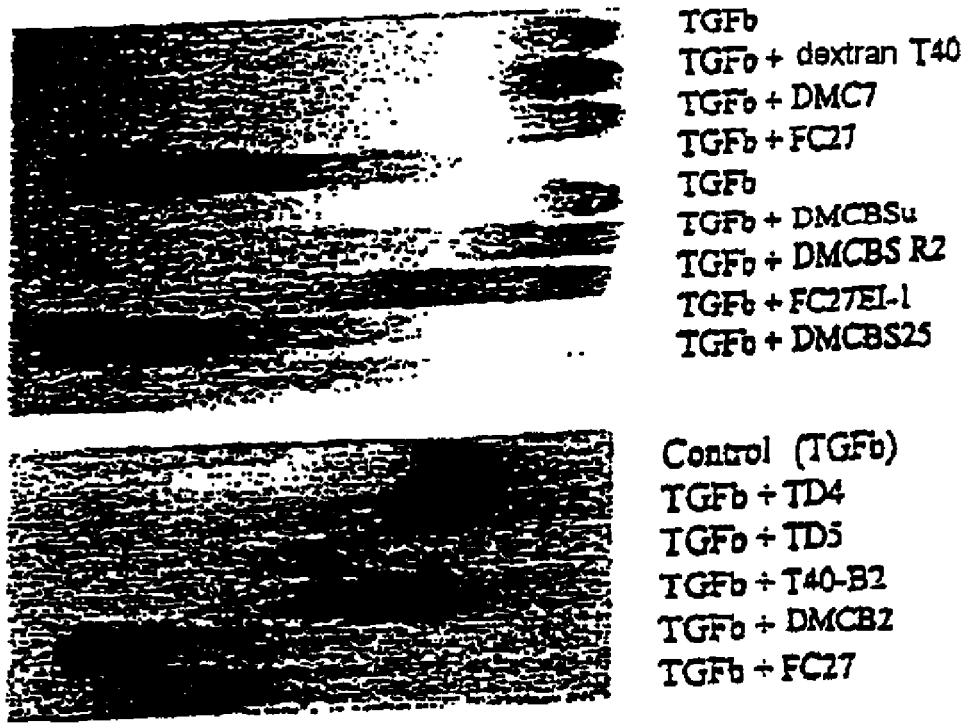
FIG. 2a represents the results of electrophoreses on 0.8% agarose gel of various polymers and of the growth factor TGF-β1.

FIG. 2a represents the results of the electrophoreses described above.

It is evident from this figure that TGF-β1 does not interact with the native dextran T40, or with DMC7, a solely carboxymethylated dextran derivative. On the other hand, TGF-β1 variably interacts with the other dextran derivatives. Two products come out of the batch: DMCB2 and FC27, for which the migration front is strongly displaced toward the anode. Their common point is a high degree of substitution with benzylamide groups. Other gel electrophoreses, not represented here, have also shown that TGF-β1 interacts with a dextran derivative substituted solely with MC (a=1.04) and Su (c=0.70) groups.

EXAMPLE 2

Demonstration of the Interaction of Various Polymers, of which Several Dextran Derivatives of Formula $DMC_aB_bSu_cS_d$, with Extracted Bovine BMP (bBMP)

As in the preceding example, this example relates to tests for screening polymers, in particular functionalized dextran derivatives in order to select polymers having good affinity for bBMP (bovine BMP).

a) Polymers Used

Cf. preceding example (table I).

b) Materials and Methods

The protocol followed is similar to the preceding example, except for the following differences:

250 ng of bBMP provided for example by Sulzer Orthopedics Biologics Inc. (Wheat Ridge, Colo.), labeled with biotin according to the Boehringer kit, are used, the electrophoresis is carried out for 2 h on 0.8% agarose gel, there is no step of incubation of the PVDF membrane with antibodies, but a step of incubation, for 2 h and at room temperature, with a solution, diluted 1/2000, of streptavidin coupled to peroxidase (that is 5 µl of streptavidin in 10 ml of TBS/0.05% Tween/1% BSA). The incubation is followed by washing of the membrane, 4×10 minutes, with a TBS/0.05% Tween solution.

c) Results

Figure 2B:
FIG. 2b represents the results of electrophoreses on 0.8% agarose gel of various polymers and of BMP extracted from a bovine bone tissue.

FIG. 2b represents the results of the electrophoreses described above. It is evident from this figure that, in a manner similar to TGF-β1 (see preceding example), bBMP does not interact with native dextran, or with a purely carboxymethylated dextran derivative. On the other hand, bBMP interacts with the other dextran derivatives tested.

EXAMPLE 3

Preparation of a Biomaterial According to the Invention a) Preparation of a Dextran Derivative Insolubilized by Sodium Trimetaphosphate (TMP)

TMP allows the crosslinking of the dextran derivative. This reaction involves phosphorylation of the polysaccharide via covalent phosphate-diester bonds, in alkaline medium. The diester bonds are created on the hydroxyl groups of the dextran. The dextran derivatives of general formula $DMC_aB_bSu_cS_d$ according to the invention having, because of their substitution, few free hydroxyl groups, their crosslinking will be carried out in the presence of native dextran (unsubstituted).

70 µl of a solution of native dextran of high molar mass (greater than or equal to 500 000 g/mol), for example dextran T500 provided by Pharmacia Fine Chemical (weight-average molar mass ($M_w$) of 464 000 g/mol, $M_w/M_n$=2.9, $M_n$ representing the number-average molar mass) are mixed with 20 µl of a solution of DMCB2 as defined in example 1 (see table I), namely a $DMC_aB_bSu_cS_d$ in which a=0.75, b=0.37 and c=d=0, said solutions being prepared in 0.5 M NaOH at concentrations of 300 mg/ml. 10 µl of a solution of TMP (that is to say $(NaPO_3)_3$) in 0.5 M NaOH at the concentration of 300 mg/ml are added to this mixture. 100 µl of a very viscous solution are thus obtained, the increase in viscosity reflecting the crosslinking of DMCB2 and dextran.

The very viscous solution obtained above is aliquoted in volumes of 1 µl on a Teflon® plate and the whole is placed in an oven at 40° C. for 2 h. The dry gels thus obtained are suspended twice for 24 h in a large excess (2 ml) of ultrapure water, in order to remove traces of sodium hydroxide from the gel, and then freeze-dried and then sterilized by ionizing radiation (25 kGray).

b) Combination of a Growth Factor (bBMP) with the Insolubilized Dextran Derivative Each gel is rehydrated under sterile conditions with 2 µl of a PBS phosphate buffer (Dubelcco formulation) containing 250 ng/ml (0.5 ng/gel) of bBMP (extracted bovine BMP, provided for example by Sulzer Orthopedics Biologics Inc, Wheat Ridge, Colo.). A biomaterial is then obtained according to the invention in the form of a hydrogel.

This hydrogel may be freeze-dried in order to preserve the biomaterial according to the invention in the form of a powder (production of 100 ready-to-use freeze-dried products from 100 µl of starting solution).

At the time of use for the preparation of an implant, the freeze-dried product may be used as it is or rehydrated with 10 µl of water for injection per mg of freeze-dried product.

The same protocol for preparing a biomaterial as described above could be carried out using a compound of general formula $DMC_aB_bSu_cS_d$ in which a=0.67, b=0.30, c=0.15 and d=0.05 (compound called FC 06).

EXAMPLE 4

Another Protocol for Preparing a Biomaterial According to the Invention a) Preparation of a Dextran Derivative Insolubilized by 1,4-butanediol-diglycidyl Ether 700 µl of a solution of dextran T500 (identical to the dextran used in the preceding example) are mixed with 200 µl of a solution of CMDBSu (cf. table I), said solutions being prepared in double distilled water, in an amount of 300 mg/ml. The resulting solution is frozen and freeze-dried.

The freeze-dried product is immersed in a solution of 1,4-butanediol-diglycidyl ether in ethyl ether (0.5% by volume) for 30 minutes at room temperature, and then the ethyl ether is evaporated at 40° C. under vacuum. The dry crosslinked gel is successively suspended in 2 ml of 0.1 M NaOH, 2 ml of double distilled water, 2 ml of 2 M NaCl and finally 3×2 ml of double distilled water. The gel is freeze-dried, and then rehydrated with 1 ml of double distilled water.

The soft gel obtained is then placed in a container consisting of a 3 cm×3 cm glass plate having an edge 1 mm high. A glass cover is placed on this container and the whole is frozen at −80° C. The ice cake obtained (3×3×0.1 cm³) is freeze-dried in the container free of its cover, and then cut with a razor blade into dry gels 5 mm along the side (that is volumes of 25 µl). The dry gels are suspended twice for 24 h in a large excess of ultrapure water (20 ml), and then freeze-dried and sterilized by ionizing radiation (25 kGray).

b) Combination of a Growth Factor (bBMP) with the Insolubilized Dextran Derivative Each gel is rehydrated under sterile conditions with 50 µl of a PBS phosphate buffer (Dubelcco formulation) containing 250 ng/ml (12.5 ng/gel) of bBMP, and then freeze-dried. About thirty ready-to-use freeze-dried products are thus obtained from 1 ml of starting solution.

At the time of use for the preparation of an implant, the freeze-dried product may be used as it is or rehydrated with 50 µl of water for injection per mg of freeze-dried product.

EXAMPLE 5

Adsorption and Release of the Growth Factor TGF-β1 by an Insolubilized Dextran Derivative of General Formula $DMC_aB_bSu_cS_d$ a) Adsorption of the Growth Factor Protocol for adsorption of TGF-β1 and for measuring the quantity of TGF-β1 adsorbed The dextran derivative called FC27 in table I is used, that is to say a dextran whose respective degrees of substitution in MC, B and Su units are 0.75, 0.37 and 0.64, said dextran being insolubilized in accordance with the protocol described in example 3. The control is a native dextran T500, which is also insolubilized as described in example 3.

In a siliconized glass tube, there are placed:

0.24 g of insolubilized FC27,

200 µl of PBS phosphate buffer comprising 0.02% of sodium azide (bactericidal agent) and 0.5% of bovine serum albumin (BSA), this compound making it possible to avoid the adsorption of the growth factor onto the walls of the glass tube, and 100 ng of TGF-β1.

The control is prepared in a similar manner, but it is from 0.30 g of native dextran and 400 µl of phosphate buffer (indeed, the dextran gel T500 has a higher swelling rate than FC27, it being possible to explain this difference by a difference in the degree of crosslinking).

The whole is left for 48 h at room temperature, with gentle stirring, and then each gel is washed with phosphate buffer in order to remove the nonabsorbed growth factor. The growth factor remaining in the tube and in the washing buffer is then assayed by the ELISA method.

Results

Table II summarizes the quantities of TGF-β1 adsorbed in the gel of functionalized dextran derivative (FC27) and in the gel of native dextran T500 (control).

TABLE II

| | Quantity of TGF-β1 adsorbed (ng) | | |
| --- | --- | --- | --- |
| Gel | Empty tube | Washing buffer | Adsorbed in the gel |
| T500 | 9.9 | 5.0 | 85.1 |
| FC27 | 13.7 | 9.4 | 76.9 |

It is evident from table II that there remains a residual TGF-β1 concentration of 14.9% to the quantity initially added for T500 and of 23.1% for FC27. Thus, T500 and FC27 respectively adsorbed 85.1% and 76.9% of the TGF-β1 initially added: the two gels significantly adsorb TGF-β1.

b) Release of the Growth Factor into a Phosphate Buffer Medium

Protocol

The kinetics of release of TGF-β1 is carried out in siliconized Swell plates. The FC27 and T500 gels in which the TGF-β1 is adsorbed are incubated in the wells in the presence of PBS phosphate buffer (either 5 ml or 10 ml, as described below), 0.02% sodium azide and 0.5% BSA, at room temperature.

The assay of TGF-β1 released into the medium is carried out by a conventional ELISA method, using 96-well microtiter plates coated with an anti-TGF-β monoclonal antibody solution (2 µg/ml) in a carbonate buffer, pH 9.6. The plate is sealed, incubated overnight at 4° C., without stirring, and then washed 5 times with 300 µl of PBS buffer, pH 7.4, comprising 0.05% of Tween 20. The blocking of the non-specific sites is then carried out with a 0.5% BSA solution (addition of 300 µl of solution per well, followed by 1 h of incubation at room temperature without stirring). After suitable washing of the wells with the washing solution described above, the standard samples (TGF-β1 range from 31.25 to 2000 pg/ml) and the test samples are prepared. Each well contains 100 µl of each sample and is incubated, with stirring, for 1 h 30 min at room temperature. After suitable washing of the plate with the washing solution described above, the wells are incubated with a solution of primary biotinylated human anti-TGF antibody at 100 ng/ml (100 µl/well) in a PBS/0.05% Tween 20/0.5% BSA buffer. After suitable washing of the plate with the washing solution described above, the wells are incubated with a solution, diluted 1/10 000 (100 µl/well), of streptavidin coupled to peroxidase. A final washing of the plate is then carried out, and then the plate is visualized with ODP (1 pastille in 25 ml of 0.05 M citrate buffer pH 5, to which 33.3 µl of hydrogen peroxide at 9% are added), adding 200 µl of reagent per well. The reaction develops for 3–4 minutes and is then stopped by adding 50 µl of 3M sulfuric acid.

To measure the kinetics of release of TGF-β1, two protocols were used:

either without change of medium, in which case 4 successive collections of samples (at 15 min, 45 min, 1 h 30 min and 8 h after immersion) of 400 µl were carried out from an initial buffer volume of 10 ml;

or with renewal of medium, in which case the initial 5 ml of buffer are collected (at 30 min, 1, 2, 5, 24 hours, 2, 3, 4, 5, 9 and 15 days) and replaced with 5 ml of fresh buffer.

Results

Figure 3A:
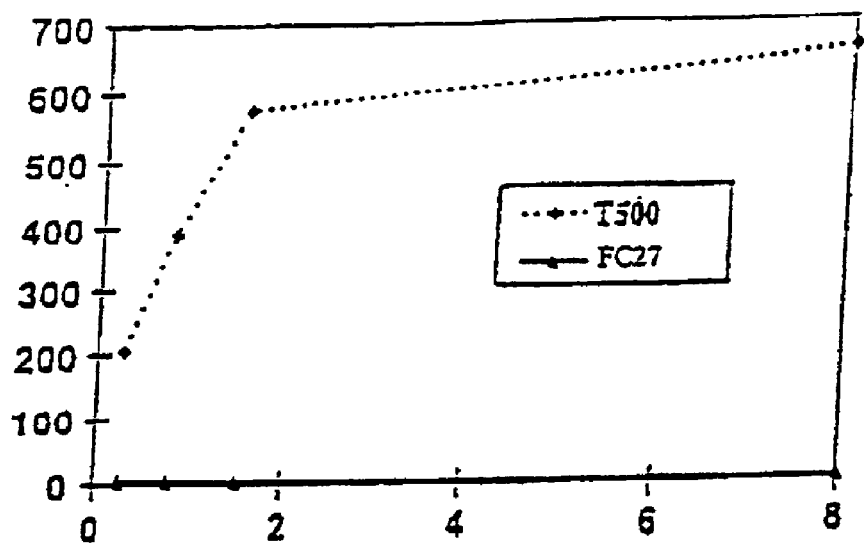
FIGS. 3a and 3b represent the quantity (in pg, cumulative values) of TGF-β1 released by the gels T500 (native dextran) and FC27 (substituted dextran derivative) as a function of time (in hours), without renewal of the medium (FIG. 3a) and with renewal of the medium (FIG. 3b), respectively, according to the protocol described in example 5.
Figure 3B:
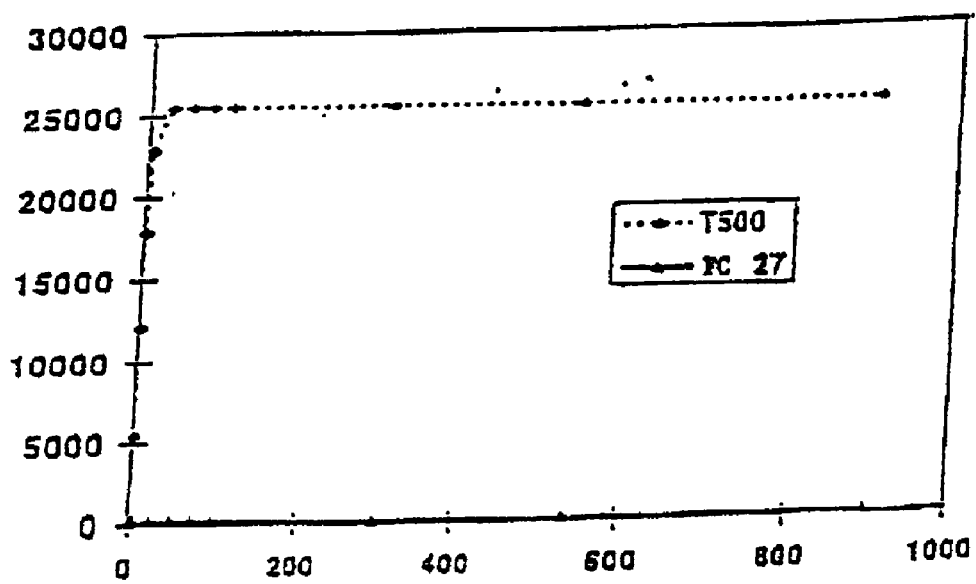

FIGS. 3a and 3b represent the quantity (in pg, cumulative values) of TGF-β1 released by the T500 and FC27 gels as a function of time (in hours), respectively without renewal of the medium (FIG. 5a) and with renewal of the medium (FIG. 5b).

These figures show a rapid release of TGF-β1 into the phosphate buffer for T500, whereas this release does not occur with FC27. It is therefore evident that FC27 forms, with TGF-β1, a complex which is not dissociated in phosphate buffer. TGF-β1 is adsorbed in the gel but is not released therefrom. It should however be specified that under in vivo conditions, the functionalized dextran gel would be exposed to various enzymes as well as to pH conditions which would promote the slow degradation of the gel and the gradual release of TGF-β1.

EXAMPLE 6

Preparation of a Bone Implant with the Aid of a Biomaterial According to the Invention in the Form of a Hydrogel For a bone cavity of about 50 mm³, 15 mg of biomaterial according to the invention are used in the form of a freeze-dried powder, as obtained in example 3, which are crushed and rehydrated with 100 µl of ultrapure water (production of a hydrogel of 100 µl).

EXAMPLE 7

Preparation of a Solid Bone Implant Comprising a Biomaterial According to the Invention Combined with a Filling Material in Particulate Form, Tricalcic Calcium Phosphate 70 µl of a solution of native dextran of high molar mass (greater than or equal to 500 000 g/mol), such as the dextran used in example 3, are mixed with 20 µl of a solution of DMCB2 (same dextran derivative as in example 3), said solutions being prepared in 0.5 M NaOH at concentrations of 300 mg/ml. 80 mg of granules (0.5 mm in diameter) of tricalcic calcium phosphate are mixed with the preceding solution and 10 µl of a solution of TMP in 0.5 M NaOH at the concentration of 300 mg/ml are added thereto. The mixture obtained is molded in the form of a cubic specimen of 5 mm³ and placed in the oven at 40° C. for 2 h.

The specimen obtained is suspended twice for 24 h in ultrapure water (100 times the volume of the cube) with gentle stirring, dried in an oven under vacuum at 40° C. overnight, and then sterilized as described in example 3.

The specimen is then rehydrated under sterile conditions with 50 µl of the PBS phosphate buffer used in example 3, containing 1 ng/µl (50 ng per specimen) of bBMP. The cube is then dried under vacuum at 40° C. for 3 h. It can be used as it is as an implant.

EXAMPLE 8

Preparation of a Coating of an Orthopedic Prosthesis with the Aid of a Biomaterial According to the Invention 210 ml of a solution of native dextran of high molar mass (greater than or equal to 500 000 g/mol), for example the dextran T500 described in example 3, are mixed with 60 ml of a solution of DMCB2 as described in example 3, said solutions being prepared in 0.5 M NaOH at concentrations of 300 mg/ml. 30 ml of a solution of TMP in 0.5 M NaOH at the concentration of 300 mg/ml are added to this mixture. The very viscous solution obtained (300 ml) is rapidly homogenized and placed at 37° C. in a suitable container.

The tail of a femoral prosthesis made of TiAl6V4 (titanium alloy comprising 6% aluminum and 4% vanadium) is immediately immersed in this mixture. It is withdrawn after 10 minutes and placed in an oven maintained at 40° C. for 2 h. The femoral tail is immersed in 1 l of ultrapure water twice for 24 h, dried in an oven under vacuum at 40° C. overnight and sterilized as described in example 3.

3 ml of a solution of the PBS buffer used in example 3, containing 300 µg of bBMP, are dispersed at the treated surface of the prosthesis in the form of a spray, under sterile conditions. The prosthesis is then dried under vacuum at 40° C. for 3 h. The prosthesis may be used as it is at the time of implantation.

The same protocol may be used to coat a knee prosthesis or an acetabulum of hip prosthesis.

EXAMPLE 9

Studies in vivo of Biomaterials According to the Invention

Protocol 0.5 cm³ of a gel of DMCB2 (dextran derivative of general formula $DMC_aB_bSu_cS_d$, in which a=0.75, b=0.37 and c=d=0) crosslinked as described in example 3 and loaded with 100 ng of extracted bovine BMP is used.

The control is a 0.5 cm³ coral cube (Porites provided by Biocoral Inc.) loaded with 100 ng of extracted bovine BMP.

The animals, 10 in number, are 3-week-old Sprague-Dawley rats weighing about 70 g. They are anesthetized with a solution of Ketalar® and Xylazine®. A particle of gel (about 1% of the initial volume of the gel) is removed with tweezers and placed intramuscularly, in the paravertebral muscles. The skin of the animals is closed with a nonresorbable suture thread. The implantation is maintained for 1 month, and then the animals are sacrificed for a histological study of the implants in the muscle mass.

Results

Figure 4A:
FIG. 4a represents a radiograph of bone neoformation induced in rats by extracted bovine BMP, according to the protocol described in example 9.

FIG. 4a represents a radiograph of the bone neoformation.

Figure 4B:
FIG. 4b represents a view under an optical microscope of a bone nodule formed at an intramuscular site in a rat, according to the protocol described in example 9.

FIG. 4b represents a view (magnification: ×100) of a newly-formed bone nodule at an intramuscular site. The mature cortical structure of the nodule can be observed.

Figure 4C:
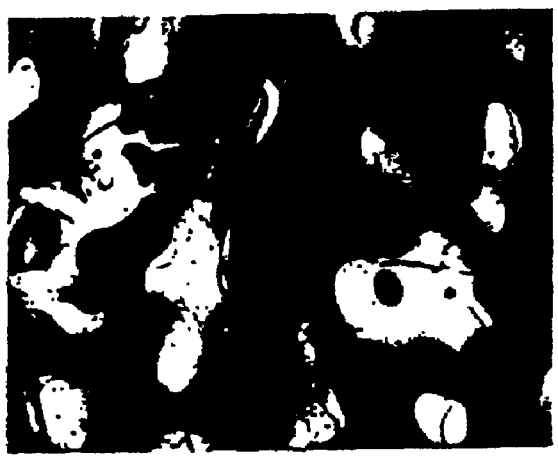
FIG. 4c represents a view under an optical microscope of an implant based on coral and extracted bovine BMP at an intramuscular site, in a rat, according to the protocol described in example 9.

FIG. 4c (magnification: ×100) represents the study control (coral charged with BMP). The porosities of the material are not very cellularized, the material is intact (no resorption) and no bone neoformation is observed.

It is evident from this study that a low dose of BMP (100 ng), vectorized by a dextran derivative of general formula $DMC_aB_bSu_cS_d$, in which a=0.75, b=0.37 and c=d=0, makes it possible to obtain a biomaterial capable of inducing bone neoformation at an ectopic site.

As is evident from the above, the invention is not at all limited to those of its embodiments, implementations and applications which have just been described more explicitly; it encompasses on the contrary all the variants which may occur to the specialist in the field without departing from the context or from the scope of the present invention.

We claim:

1. A solid biomaterial, characterized in that it comprises:
   (1) at least one solid support material consisting of at least one crosslinked insolubilized dextran derivative of general formula $DMC_aB_bSu_cS_d$ in which:

D represents a polysaccharide chain, preferably consisting of successions of glucoside units, MC represents methyl carboxylate groups, B represents carboxymethylbenzylamide groups, Su represents sulfate groups, S represents sulfonate groups, a, b, c and d represent the degree of substitution (ds), expressed relative to the number of free hydroxyl functional groups in a glucoside unit of the dextran, respectively in MC, B, Su and S groups; a being $\geq 0.3$, b being equal to 0 or $\geq 0.2$, c being equal to 0 or $\geq 0.1$ and d being equal to 0 or $\leq 0.15$, provided that when b is equal to 0, c is not equal to 0, and (2) at least one growth factor exhibiting activity on the osteoarticular tissues, the dental tissues and/or the maxillofacial tissues.

2. The biomaterial as claimed in claim 1, characterized in that said insolubilized dextran derivative is such that d is equal to 0.

3. The biomaterial as claimed in claim 1, characterized in that said growth factor is selected from the group consisting of Epidermic Growth Factors (EGFs), Insulin-like Growth Factors (IGFs), Fibroblast Growth Factors (FGFs), Transforming Growth Factors (TGF-βs), Platelet-Derived Growth Factors (PDGFs) and Bone Morphogenic Proteins (BMPs).

4. The biomaterial as claimed in claim 1, characterized in that said growth factor has an osteoinductive activity and is a BMP.

5. The biomaterial as claimed in claim 1, characterized in that it comprises insolubilized dextran derivatives and/or growth factors involved in the bone reconstruction process.

6. The biomaterial as claimed in claim 1, characterized in that it is insolubilized by crosslinking with the aid of a crosslinking agent.

7. The biomaterial as claimed in claim 6, characterized in that said crosslinking agent is selected from the group consisting of sodium trimetaphosphate, epichlorohydrin, divinyl sulfone, gluteraldehyde and bisepoxiranes.

8. The biomaterial as claimed in claim 1, characterized in that it exists in the form of a hydrogel.

9. The biomaterial as claimed in claim 1, characterized in that it exists in the form of a freeze-dried powder.

10. The biomaterial as claimed in claim 9, characterized in that said freeze-dried powder is obtained from biomaterial existing in the form of a hydrogel.

11. The biomaterial as claimed in claim 1, characterized in that it comprises, in addition, a tissue filling material.

12. The biomaterial as claimed in claim 11, characterized in that it coats particles of an inorganic or polymeric insoluble support, said particles having a diameter greater than 100 μm.

13. The biomaterial as claimed in claim 11, characterized in that said tissue filling material is selected from the group consisting of collagen, gelatin, biological adhesive, polymers of polylactic or polyglycolic acids and copolymers of polyethylene glycol with polylactide-co-glycolide.

14. The biomaterial as claimed in claim 11, characterized in that said tissue filling material is an osteoconductive material selected from the group consisting of coral, hydroxyapatite, a mixture of collagen and hydroxyapatite, tricalcium phosphate, calcium sulfate and calcium carbonate.

15. A process for preparing the solid biomaterial as claimed in claim 3, characterized in that the process comprises the following steps:

crosslinking of at least one dextran derivative of general formula $DMC_aB_bSu_cS_d$ as defined in claim 3, adsorption, in the insolubilized dextran derivative obtained above, of at least one growth factor as defined in claim 3, production of a solid biomaterial according to claim 3 in the form of a hydrogel, optionally, the freeze-drying of said hydrogel in order to obtain said biomaterial in the form of a powder.

16. The process as claimed in claim 15, characterized in that said crosslinking of at least one dextran derivative of general formula $DMC_aB_bSu_cS_d$ is carried out with the aid of a crosslinking agent selected from the group consisting of sodium trimétaphosphate, epichlorohydrin, divinyl sulfone, glutaraldéhyde and bisepoxiranes.

17. The process as claimed in claim 15, characterized in that the crosslinking of at least one dextran derivative of general formula $DMC_aB_bSu_cS_d$ is carried out in the presence of a tissue filling material.

18. The process as claimed in claim 17, characterized in that said tissue filling material is selected from the group consisting of collagen, gelatin, biological adhesive, polymers of polylactic or polyglycolic acids, copolymers of polyethylene glycol with polylactide-co-glycolide, and an osteoconductive material selected form the group consisting of coral, hydroxyapatite, a mixture of collagen and hydroxyapatite, tricalcium phosphate, calcium sulfate, and calcium carbonate.

19. A process for preparing the biomaterial as claimed in claim 12, characterized in that it comprises the following steps:

bringing the dextran derivative into contact with particles of an inorganic or polymeric insoluble support, as defined in claim 12, so as to obtain a composite, crosslinking of the composite obtained above, with a crosslinking agent, adsorption, in the insolubilized composite obtained above, of at least one of said growth factors.

20. An osteoarticular, dental or maxillofacial implant, or a coating for orthopedic, dental or maxillofacial prosthesis wherein said implant or coating is made of a solid material according to claim 1.

21. A prosthesis, characterized in that at least part of its surface is coated with a solid biomaterial as claimed in claim 1.

* * * * *

UNITED STATES PATENT AND TRADEMARK OFFICE
CERTIFICATE OF CORRECTION

| | | |
|---|---|---|
| PATENT NO. | : 6,946,443 B2 | Page 1 of 1 |
| APPLICATION NO. | : 10/016706 | |
| DATED | : September 20, 2005 | |
| INVENTOR(S) | : Cinderella Blanchat et al. | |

It is certified that error appears in the above-identified patent and that said Letters Patent is hereby corrected as shown below:

Title page, item (22), correct "Filed: Dec. 11, 2001" to
-- PCT Filed: Jun. 9, 2000 --

Title page, add the following:
-- (86) PCT No.: PCT/FR00/01603 --

Title page, add the following:
-- (87) PCT Pub. No.: WO00/76562 A1
PCT Pub. Date: Dec. 21, 2000 --

Title page, add the following:
-- (30) Foreign Application Priority Data
Jun. 11, 1999 (FR) 99/07401 --

Signed and Sealed this

Twenty-sixth Day of December, 2006

JON W. DUDAS
*Director of the United States Patent and Trademark Office*